US009180085B2

(12) United States Patent
Braun et al.

(10) Patent No.: US 9,180,085 B2
(45) Date of Patent: Nov. 10, 2015

(54) INVERSE LATICES BASED ON FATTY ALCOHOL ETHERS, AND COSMETIC, DERMOCOSMETIC, DERMOPHARMACEUTICAL OR PHARMACEUTICAL COMPOSITIONS COMPRISING

(75) Inventors: Olivier Braun, Castres (FR); Paul Mallo, Croissy-sur-Seine (FR); Hervé Rolland, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 1292 days.

(21) Appl. No.: 12/994,978

(22) PCT Filed: Jun. 22, 2009

(86) PCT No.: PCT/FR2009/051189
§ 371 (c)(1),
(2), (4) Date: Nov. 29, 2010

(87) PCT Pub. No.: WO2009/156690
PCT Pub. Date: Dec. 30, 2009

(65) Prior Publication Data
US 2011/0098364 A1    Apr. 28, 2011

(30) Foreign Application Priority Data
Jun. 27, 2008    (FR) ...................................... 08 54321

(51) Int. Cl.
| | |
|---|---|
| A61K 8/81 | (2006.01) |
| A61K 8/33 | (2006.01) |
| A61Q 19/00 | (2006.01) |
| C08G 65/332 | (2006.01) |
| C08L 71/02 | (2006.01) |
| A61Q 1/02 | (2006.01) |
| A61Q 1/04 | (2006.01) |
| A61Q 1/12 | (2006.01) |
| A61Q 1/14 | (2006.01) |
| A61Q 5/00 | (2006.01) |
| A61Q 5/02 | (2006.01) |
| A61Q 17/04 | (2006.01) |
| A61Q 19/04 | (2006.01) |
| C08K 5/06 | (2006.01) |

(52) U.S. Cl.
CPC ................ *A61K 8/8158* (2013.01); *A61K 8/33* (2013.01); *A61Q 19/00* (2013.01); *C08G 65/3322* (2013.01); *C08L 71/02* (2013.01); *A61K 2800/48* (2013.01); *A61Q 1/02* (2013.01); *A61Q 1/04* (2013.01); *A61Q 1/12* (2013.01); *A61Q 1/14* (2013.01); *A61Q 5/00* (2013.01); *A61Q 5/02* (2013.01); *A61Q 17/04* (2013.01); *A61Q 19/002* (2013.01); *A61Q 19/004* (2013.01); *A61Q 19/04* (2013.01); *C08K 5/06* (2013.01); *C08L 2205/05* (2013.01)

(58) Field of Classification Search
CPC ............................... A61K 8/33; A61K 8/8158
USPC ........................................................ 514/772.1
See application file for complete search history.

(56) References Cited

U.S. PATENT DOCUMENTS

| | | | |
|---|---|---|---|
| 6,136,305 | A | 10/2000 | Michel-Lecocu et al. |
| 6,197,287 | B1 | 3/2001 | Mallo et al. |
| 6,375,959 | B1 | 4/2002 | Mallo et al. |
| 2002/0032243 | A1 | 3/2002 | Tabacchi et al. |

FOREIGN PATENT DOCUMENTS

| | | |
|---|---|---|
| EP | 0503853 A2 | 9/1992 |
| EP | 0716594 B1 | 10/2001 |
| EP | 1166771 A1 | 1/2002 |
| EP | 1056805 B2 | 3/2004 |
| EP | 1047716 B1 | 12/2006 |
| FR | 2903005 A1 | 1/2008 |

OTHER PUBLICATIONS

International Search Report, dated Jan. 21, 2010, from corresponding PCT application.

*Primary Examiner* — Jake Vu
(74) *Attorney, Agent, or Firm* — Young & Thompson

(57) ABSTRACT

Novel inverse latices based on fatty alcohol ethers of formula $R_1$—O—$R_2$ (I) in which $R_1$ and $R_2$ represent, independently from one another, a linear or branched alkyl radical comprising from 5 to 18 carbon atoms; and cosmetic, dermocosmetic, dermopharmaceutical or pharmaceutical compositions comprising them.

9 Claims, No Drawings

INVERSE LATICES BASED ON FATTY ALCOHOL ETHERS, AND COSMETIC, DERMOCOSMETIC, DERMOPHARMACEUTICAL OR PHARMACEUTICAL COMPOSITIONS COMPRISING

The present patent application relates to water-in-oil inverse latices, to the method for preparing same and to the use thereof as thickeners and/or emulsifiers for skin, hair and scalp care products and for the production of cosmetic, dermocosmetic, dermopharmaceutical or pharmaceutical preparations.

Synthetic thickening polymers, in the form of inverse latices, are described as being able to be used in the production of topical compositions, in the European patent applications published under the numbers EP 0 716 594, EP 1 047 716, EP 1 056 805 and EP 0 503 853.

However, some of them sometimes create intolerance reactions on certain sensitive skins.

In order to limit such undesirable effects, attempts have sometimes been made to replace the mineral oils commonly used as organic phase of these inverse latices with plant oils, as is, for example, described in the European patent application published under the number 1 166 771. However, such a use causes, in certain cases, an accelerated sedimentation of the inverse latex and, in other cases, a decrease in, or even blocking of, its inversion when it is introduced into an aqueous phase.

For this reason, the inventors have focused on the search for new polymer emulsions which are better tolerated by the skin while at the same time inverting satisfactorily.

The subject of the invention is a composition in the form of an inverse latex comprising, for 100% of its mass:
a) from 10% by mass to 80% by mass of a linear, branched or crosslinked polymer (P) of 2-methyl-2-[(1-oxo-2-propenyl)amino]-1-propanesulfonic acid (also known as 2-acrylamido-2-methylpropanesulfonic acid) which is partially or totally salified, and of optionally one or more monomers chosen from acrylic acid, methacrylic acid, itaconic acid, maleic acid or 3-methyl-3-[(1-oxo-2-propenyl)amino]butanoic acid, the carboxylic function of said monomers being in acid form, partially salified or totally salified, acrylamide, methacrylamide, diacetone-acrylamide, N,N-dimethylacrylamide, N-isopropyl-acrylamide, N-[2-hydroxy-1,1-bis(hydroxymethyl)-ethyl]propenamide [or tris(hydroxymethyl)acrylamido-methane or N-tris(hydroxymethyl)methylacrylamide also known as THAM], (2-hydroxyethyl)acrylate, (2,3-dihydroxypropyl)acrylate, (2-hydroxyethyl)methacrylate, (2,3-dihydroxypropyl)methacrylate, an ethoxylated derivative, of molecular weight between 400 and 1000, of each of these esters or vinylpyrrolidone; 2,N,N,N-tetramethyl-2-[(1-oxo-2-propenyl)amino]propanammonium chloride, bromide or iodide, 2,N,N-trimethyl-2-[(1-oxo-2-propenyl)amino]-propanammonium chloride, bromide or iodide, N,N,N-trimethyl-2-[(1-oxo-2-propenyl)oxy]ethanammonium chloride, bromide or iodide, N,N,N-trimethyl-3-[(1-oxo-2-propenyl)oxy]propanammonium chloride, bromide or iodide, N,N,N-trimethyl-2-[(1-oxo-2-propenyl)-amino]propanammonium chloride, bromide or iodide, or diallyldimethylammonium chloride, bromide or iodide;
b) from 5% by mass to 10% by mass of an emulsifying system ($S_1$) of water-in-oil (W/O) type,
c) from 1% by mass to 50% by mass of water,
d) from 5% by mass to 50% by mass of at least one compound chosen from the compounds of formula (I):

$$R_1\text{—}O\text{—}R_2 \qquad (I),$$

in which $R_1$ and $R_2$ represent, independently of one another, a linear or branched alkyl radical containing from 5 to 18 carbon atoms.

In the composition as defined above, the polymer (P) present in the composition which is the subject of the invention may be a homopolymer or a polymer formed from several different types of monomers. It is mainly a homopolymer, a copolymer, a terpolymer or a tetrapolymer.

The term "branched polymer" denotes, for (P), a nonlinear polymer which has pendent chains so as to obtain, when this polymer is dissolved in water, a high state of entanglement leading to very high low-gradient viscosities.

The term "crosslinked polymer" denotes, for (P), a nonlinear polymer which is in the form of a three-dimensional network that is water-insoluble but water-swellable and which thus leads to the production of a chemical gel.

According to one particular aspect of the present invention, in the polymer (P) as defined above, the molar proportion of 2-methyl-2-[(1-oxo-2-propenyl)-amino]-1-propanesulfonic acid monomeric unit is greater than or equal to 30%, and more particularly greater than or equal to 40%.

The composition according to the invention may comprise a linear polymer, a crosslinked polymer or a branched polymer.

According to one particular aspect of the present invention, the polymer (P) is crosslinked.

When the polymer (P) is crosslinked, it is more particularly crosslinked with a diethylene or polyethylene compound in a molar proportion, expressed relative to the total molar amount of monomers used, of less than or equal to 0.25% and more particularly less than or equal to 0.05%, and most particularly between 0.005% and 0.01%. Preferably, the crosslinking agent and/or the branching agent is chosen from ethylene glycol dimethacrylate, diethylene glycol diacrylate, ethylene glycol diacrylate, diallylurea, triallylamine, trimethylolpropane triacrylate, methylenebis (acrylamide) or a mixture of these compounds, diallyloxyacetic acid or one of its salts, such as sodium diallyloxyacetate, or a mixture of these compounds.

For the constituent monomers comprising an acid function, of the polymer (P) of the composition as defined above, the term "salified" indicates that it is a question of alkali metal salts, such as sodium or potassium salts, or salts of nitrogenous bases, for instance the ammonium salt, the lysine salt or the monoethanolamine salt ($HO\text{—}CH_2\text{—}CH_2\text{—}NH_4^+$).

According to one particular aspect of the present invention, the term "salified" signifies that the acid function is salified in the form of a sodium salt.

In the composition as defined above, the emulsifying system ($S_1$) of water-in-oil (W/O) type consists either of a sole emulsifying surfactant or of a mixture of emulsifying surfactants, provided that said mixture has an HLB value that is sufficiently low to generate water-in-oil emulsions. As emulsifying surfactants of water-in-oil type, mention may be made, for example, of sorbitan esters, such as sorbitan oleate, for instance the product sold by the company SEPPIC under the name Montane™ 80, sorbitan isostearate, for instance the product sold by the company SEPPIC under the name Montane™ 70, or sorbitan sesquioleate, for instance the product sold by the company SEPPIC under the name Montane™ 83. Mention may also be made of certain polyethoxylated sorbitan esters, for example pentaethoxylated sorbitan monooleate, for instance the product sold by the company SEPPIC under the name Montanox™ 81, or pentaethoxylated sorbitan isostearate, for instance the product sold under the name Montanox™ 71 by the company SEPPIC. Mention may also be made of diethoxylated oleocetyl alcohol, for instance the product sold under the name Simulsol™ OC 72 by the company SEPPIC, polyesters with a molecular weight of between 1000 and 3000, products resulting from condensation between a poly(isobutenyl)succinic acid or the anhydride thereof, such as Hypermer™ 2296 sold by the company Uniqema or else polyglycerol polyhydroxystearate (Dehymuls™ PGPH sold by the company Cognis) or, finally, block copolymers with a molecular weight of between 2500 and 3500, such as Hypermer™ B246 sold by the company Uniqema or Simaline™ IE 200 sold by the company SEPPIC.

According to one particular aspect of the composition as defined above, the latter also comprises:

e) up to 5% by mass of an emulsifying system ($S_2$) of oil-in-water (O/W) type.

The emulsifying system ($S_2$) of oil-in-water (O/W) type used in the particular aspect of the composition as defined above consists either of a sole emulsifying surfactant or of a mixture of emulsifying surfactants, provided that said mixture has an HLB value that is sufficiently high to provide oil-in-water emulsions. As emulsifying surfactants of oil-in-water type, mention may be made, for example, of ethoxylated sorbitan esters, for instance sorbitan oleate polyethoxylated with 20 mol of ethylene oxide, sold by the company SEPPIC under the name Montanox™ 80, sorbitan laurate polyethoxylated with 20 mol of ethylene oxide, sold by the company SEPPIC under the name Montanox™ 20, sorbitan stearate polyethoxylated with 20 mol of ethylene oxide, sold by the company SEPPIC under the name Montanox™ 60, castor oil polyethoxylated with 40 mol of ethylene oxide, sold under the name Simulsol™ OL50, decaethoxylated oleodecyl alcohol, sold by the company SEPPIC under the name Simulsol™ OC 710, heptaethoxylated lauryl alcohol sold by the company SEPPIC under the name Simulsol™ P7, decaethoxylated nonylphenol sold by the company SEPPIC under the name Nonarox™ 1030 or the polyethoxylated sorbitan hexaoleates sold by the company SEPPIC under the name Simaline™ IE 400.

As other emulsifying surfactants of oil-in-water type, mention may also be made of the compounds of formula (II):

$$R_4\text{—}O\text{-}(G)_x\text{-}H \qquad (II)$$

in which $R_4$ represents a saturated or unsaturated, linear or branched aliphatic hydrocarbon-based radical containing from 1 to 30 carbon atoms, G represents the glucose residue or the xylose residue, and x represents a decimal number between 1.05 and 2.5.

The oligomeric structure $(G)_x$ may be in any form of isomerism, whether it is optical isomerism, geometric isomerism or positional isomerism; it may also represent a mixture of isomers. In formula (II) as defined above, the $R_4$—O— radical is bonded to G via the anomeric carbon so as to form an acetal function. The number x, which represents, in formula (II), the average degree of polymerization of the saccharide, is more particularly between 1.1 and 2.0. As emulsifying surfactants of oil-in-water type, mention may more particularly be made of the compounds of formula (II) as defined above, in which $R_4$ represents a radical comprising from 8 to 18 carbon atoms, and most particularly in which $R_4$ represents more particularly an octyl, decyl, undecyl, dodecyl, tetradecyl or hexadecyl radical, said radicals being linear or branched. As examples of commercial products containing said compounds of formula (II), mention may be made, for example, of:

Simulsol™ SL8, sold by the company SEPPIC, which is an aqueous solution containing, for 100% of its total mass, between approximately 58% and 62% by mass of a mixture of alkyl polyglycosides consisting of, for 100% of its total mass, between 45% by mass and 55% by mass of a compound of formula (II), in which G represents the glucose residue, x is equal to approximately 1.45, n is equal to 0 and $R_4$ represents a decyl radical, and between 45% by mass and 55% by mass of a compound of formula (II), in which G represents the glucose residue, x is equal to approximately 1.45, n is equal to 0 and $R_4$ represents an octyl radical;

Simulsol™ SL10, sold by the company SEPPIC, which is an aqueous solution containing, for 100% of its total mass, between approximately 53% by mass and 57% by mass of a mixture of alkyl polyglycosides consisting of, for 100% of its total mass, approximately 85% by mass of a compound of formula (II), in which G represents the glucose residue, x is equal to approximately 1.45, n is equal to 0 and $R_4$ represents a decyl radical, approximately 7.5% by mass of a compound of formula (II), in which G represents the glucose residue, x is equal to approximately 1.45, n is equal to 0 and $R_4$ represents a dodecyl radical, and approximately 7.5% by mass of a compound of formula (II), in which G represents the glucose residue, x is equal to approximately 1.45, n is equal to 0 and $R_4$ represents a tetradecyl radical;

Simulsol™ SL11 W, sold by the company SEPPIC, which is an aqueous solution containing, for 100% of its total mass, between approximately 53% by mass and 57% by mass of a mixture of alkyl polyglycosides of formula (II), in which G represents the glucose residue, x is equal to approximately 1.45, n is equal to 0 and $R_4$ represents a mixture of isodecyl, isoundecyl and isododecyl radicals; or Simulsol™ SL26, sold by the company SEPPIC, which is an aqueous solution containing, for 100% of its total mass, between approximately 50% by mass and 55% by mass of a mixture of alkyl polyglycosides consisting of, for 100% of its total mass, approximately 70% by mass of a compound of formula (II), in which G represents the glucose residue, x is equal to approximately 1.45, n is equal to 0 and $R_4$ represents a dodecyl radical, approximately 25% by mass of a compound of formula (II), in which G represents the glucose residue, x is equal to approximately 1.45, n is equal to 0 and $R_4$ represents a tetradecyl radical, and approximately 5% by mass of a compound of formula (II), in which G represents the glucose residue, x is equal to approximately 1.45, n is equal to 0 and $R_4$ represents a hexadecyl radical.

As other emulsifying surfactants of oil-in-water type, mention may also be made of the compounds of formula (III):

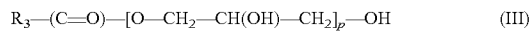

$$R_3\text{—}(C\!\!=\!\!O)\text{—}[O\text{—}CH_2\text{—}CH(OH)\text{—}CH_2]_p\text{—}OH \qquad (III)$$

in which $R_3$ represents a linear or branched aliphatic radical containing from 5 to 17 carbon atoms and p an integer of greater than or equal to 3 and less than or equal to 20.

As particular examples of such compounds, mention may be made of those of formula (IIIa) corresponding to formula (III) as defined above, in which $R_3$ represents a linear or branched aliphatic radical containing from 11 to 17 carbon atoms.

As other particular examples of such compounds, mention may be made of those of formula (IIIb) corresponding to formula (III) as defined above, in which p is equal to 10.

As examples of commercial products containing said compounds of formulae (III), (IIIa) and/or (IIIb), mention may be made, for example, of:

Polyado™ 10-1-O KFG sold by the company Lonza, consisting essentially of decaglyceryl monooleate;

Nikkol™ Decaglyn™ 1-IS sold by the company Nikko Chemicals, consisting essentially of decaglyceryl monoisostearate;

Nikkol™ Decaglyn™ 1-L sold by the company Nikko Chemicals, consisting essentially of decaglyceryl monolaurate;

Nikkol™ Decaglyn™ 1-LN sold by the company Nikko Chemicals, consisting essentially of decaglyceryl monolinoleate;

Nikkol™ Decaglyn™ 1-M sold by the company Nikko Chemicals, consisting essentially of decaglyceryl monomyristate;

Drewpol™ 10-1 CCK sold by the company Stepan, consisting essentially of decaglyceryl monocaprylate.

According to one particular aspect of the present invention, the inverse latex also comprises up to 30% by mass of co-surfactants such as, for example, sorbitan laurate.

According to another particular aspect, the composition as defined above comprises from 20% by mass to 70% by mass of said polymer, and more particularly from 30% by mass to 50% by mass.

According to another particular aspect of the composition as defined above, in formula (I), $R_1$ and $R_2$ represent in particular, independently of one another, an alkyl radical chosen from pentyl, hexyl, 1,3-dimethylbutyl, heptyl, octyl, nonyl, isononyl, decyl, undecyl, dodecyl, tetradecyl, hexadecyl or octadecyl radicals.

According to a more particular aspect of the composition as defined above, the compound of formula (I) is chosen from the following compounds:

Dioctyl ether, didecyl ether, didodecyl ether, dodecyl octyl ether, dihexadecyl ether, (1,3-dimethylbutyl) tetradecyl ether, (1,3-dimethylbutyl) hexadecyl ether, bis(1,3-dimethylbutyl) ether and dihexyl ether.

The constitutive ethers of the oil phase of the inverse latex which is a subject of the present invention are commercially available or can be prepared by methods known to those skilled in the art, for instance the method described in the European patent published under number EP 0 753 500 B1.

According to another particular aspect of the present invention, the polymer (P) included in the inverse latex as defined above is chosen from:

a homopolymer of 2-methyl-2-[(1-oxo-2-propenyl)-amino]-1-propanesulfonic acid partially or totally salified in the form of a sodium salt or of an ammonium salt;

a copolymer of 2-methyl-2-[(1-oxo-2-propenyl)amino]-1-propanesulfonic acid, partially or totally salified in the form of a sodium salt or an ammonium salt, and of (2-hydroxyethyl)acrylate;

a copolymer of 2-methyl-2-[(1-oxo-2-propenyl)amino]-1-propanesulfonic acid and of acrylic acid partially or totally salified in the form of a sodium salt or of an ammonium salt;

a copolymer of 2-methyl-2-[(1-oxo-2-propenyl)amino]-1-propanesulfonic acid partially or totally salified in the form of a sodium salt or of an ammonium salt, and of acrylamide;

a copolymer of 2-methyl-2-[(1-oxo-2-propenyl)amino]-1-propanesulfonic acid partially or totally salified in the form of a sodium salt or of an ammonium salt, and of N,N-dimethylacrylamide;

a terpolymer of 2-methyl-2-[(1-oxo-2-propenyl)amino]-1-propanesulfonic acid partially or totally salified in the form of a sodium salt or of an ammonium salt, of acrylamide and of vinylpyrrolidone;

a terpolymer of 2-methyl-2-[(1-oxo-2-propenyl)amino]-1-propanesulfonic acid partially or totally salified in the form of a sodium salt or of an ammonium salt, of acrylic acid partially or totally salified in the form of a sodium salt or of an ammonium salt, and of acrylamide;

a terpolymer of 2-methyl-2-[(1-oxo-2-propenyl)amino]-1-propanesulfonic acid partially or totally salified in the form of a sodium salt or of an ammonium salt, of acrylic acid partially or totally salified in the form of a sodium salt or of an ammonium salt, and of N,N-dimethylacrylamide;

a tetrapolymer of 2-methyl-2-[(1-oxo-2-propenyl)-amino]-1-propanesulfonic acid partially or totally salified in the form of a sodium salt or of an ammonium salt, of (2-hydroxyethyl)acrylate, of acrylic acid partially or totally salified in the form of a sodium salt or of an ammonium salt, and of N-[2-hydroxy-1,1-bis(hydroxymethyl)ethyl]propenamide.

According to a more particular aspect of the present invention, the polymer (P) is chosen from:

a crosslinked copolymer of 2-methyl-2-[(1-oxo-2-propenyl)amino]-1-propanesulfonic acid (a) partially or totally salified in the form of a sodium salt, and of (2-hydroxyethyl)acrylate (b), in an (a)/(b) molar ratio between 30/90 and 90/10, and more particularly between 40/60 and 90/10;

a crosslinked copolymer of 2-methyl-2-[(1-oxo-2-propenyl)amino]-1-propanesulfonic acid (a) partially or totally salified in the form of a sodium salt, and of acrylic acid (c) partially or totally salified in the form of a sodium salt, in an (a)/(c) molar ratio of greater than 30/70 and 90/10, and more particularly between 40/60 and 90/10, and most particularly greater than 55/45;

a crosslinked copolymer of 2-methyl-2-[(1-oxo-2-propenyl)amino]-1-propanesulfonic acid (a) partially or totally salified in the form of a sodium salt, and of acrylamide (d), in an (a)/(d) molar ratio of greater than 30/70 and 90/10, and more particularly between 40/60 and 90/10, and most particularly greater than or equal to 50/50;

a crosslinked copolymer of 2-methyl-2-[(1-oxo-2-propenyl)amino]-1-propanesulfonic acid (a) partially or totally salified in the form of a sodium salt, and of N,N-dimethylacrylamide (e), in an (a)/(e) molar ratio of greater than 30/70 and 90/10, and more particularly between 40/60 and 90/10, and most particularly greater than or equal to 50/50;

a crosslinked terpolymer of 2-methyl-2-[(1-oxo-2-propenyl)amino]-1-propanesulfonic acid (a) partially or totally salified in the form of a sodium salt, of acrylamide (d) and of vinylpyrrolidone (f), in an (a)/[(d)+(f)] molar ratio of greater than 30/70 and 90/10, and more particularly between 40/60 and 90/10, and most particularly greater than or equal to 50/50;

a crosslinked terpolymer of 2-methyl-2-[(1-oxo-2-propenyl)amino]-1-propanesulfonic acid (a) partially or totally salified in the form of a sodium salt, of acrylic acid (c) partially or totally salified in the form of a sodium salt, and of acrylamide (d), in an (a)/[(c)+(d)] molar ratio of greater than 30/70 and 90/10 and more particularly between 40/60 and 90/10, and most particularly greater than 55/45;

a crosslinked terpolymer of 2-methyl-2-[(1-oxo-2-propenyl)amino]-1-propanesulfonic acid (a) partially or totally salified in the form of a sodium salt, of acrylic acid (c) partially or totally salified in the form of a sodium salt, and of N,N-dimethylacrylamide (e), in an (a)/(e) molar ratio of greater than 30/70 and 90/10, and more particularly between 40/60 and 90/10, and most particularly greater than or equal to 50/50;

a crosslinked tetrapolymer of 2-methyl-2-[(1-oxo-2-propenyl)amino]-1-propanesulfonic acid (a) partially or totally salified in the form of a sodium salt, of (2-hydroxyethyl)acrylate (b), of acrylic acid (c) partially or totally salified in the form of a sodium salt, and of N-[2-hydroxy-1,1-bis(hydroxymethyl)-ethyl]propenamide (g), in an (a)/[(b)+(c)+(g)] molar ratio of greater than 30/70 and less than or equal to 90/10, and more particularly between 40/60 and 90/10, and most particularly greater than or equal to 50/50.

The inverse latex as defined above generally contains from 4% to 10% by weight of emulsifiers. Generally, from 20% to 50%, and more particularly from 25 to 40%, of the total weight of the emulsifiers is of the water-in-oil type and from 80% to 50%, and more particularly from 75% to 60%, is of the oil-in-water type.

The inverse latex as defined above generally contains from 5% to 50%, and preferably from 20% to 25%, of compound of formula (I) as defined above. This latex can also contain one or more additives chosen, in particular, from complexing agents, transfer agents or chain limiters.

The inverse latex as defined above generally contains from 1% by mass to 40% by mass of water.

The inverse latex which is the subject of the present invention is generally prepared by inverse emulsion polymerization, a method known to those skilled in the art.

If necessary or if desired, the water-in-oil emulsion of polymer obtained at the end of the polymerization step can be concentrated in order to remove the desired amount of water, and said emulsifying system ($S_2$) of oil-in-water (O/W) type and/or said co-surfactant can be added to said emulsion.

The subject of the invention is also the use of the composition as defined above, for preparing a cosmetic, dermopharmaceutical or pharmaceutical topical composition.

A topical composition according to the invention, intended to be applied to the skin, to the hair, to the scalp or to the mucous membranes of humans or animals, can consist of a topical emulsion comprising at least one aqueous phase and at least one oily phase. This topical emulsion may be of the oil-in-water type. More particularly, this topical emulsion can consist of a fluid emulsion, such as a milk or a fluid gel. The oily phase of the topical emulsion can consist of a mixture of one or more oils.

A topical composition according to the invention may be intended for a cosmetic use or be used for preparing a medicament for use in the treatment of skin, scalp and mucous membrane diseases. In the latter case, the topical composition then comprises an active ingredient which can, for example, consist of an anti-inflammatory agent, a muscle relaxant, an antifungal agent or an antibacterial agent.

When the topical composition is used as a cosmetic composition intended to be applied to the skin, the scalp or the mucous membranes, it may optionally comprise an active ingredient, for example a moisturizer, a tanning agent, a sunscreen, an anti-wrinkle agent, a slimming agent, a free-radical scavenger, an anti-acne agent or an antifungal agent.

A topical composition according to the invention usually comprises, for 100% of its total mass, between 0.1% and 10% by mass of the thickener defined above. The pH of the topical composition is preferably greater than or equal to 5.

The topical composition may also comprise compounds conventionally included in compositions of this type, for example fragrances, preservatives, antioxidants, dyes, emollients or surfactants.

According to yet another aspect, the invention relates to the use of the novel thickener in accordance with the invention, mentioned above, for thickening and emulsifying a topical composition comprising at least one aqueous phase.

The composition according to the invention is an advantageous substitute for those sold under the names Sepigel™ 305, Sepigel™ 501, Simulgel™ EG, Simulgel™ NS, Simulgel™ INS 100, Simulgel™ SMS 88, Simulgel™ S, Sepiplus 400, Sepiplus 265, Sepiplus S or Simulgel™ 600 by the applicant, since it also exhibits good compatibility with the other excipients used for the preparation of formulations such as milks, lotions, creams, soaps, bubblebath, balms, shampoos or conditioners. It can also be used with said Sepigel or Simulgel products.

It is in particular compatible with the concentrates described and claimed in international publications WO 92/06778, WO 95/04592, WO 95/13863, WO 96/37285, WO 98/22207 and WO 98/47610 or in FR 2734 496, and with the surfactants described in WO 93/08204.

It is particularly compatible with Montanov™ 68, Montanov™ 82, Montanov™ 202, Montanov™ 14, Montanov™ L or Montanov™ S. It can also be used in emulsions of the type described and claimed in EP 0 629 396 and in the cosmetically or physiologically acceptable aqueous dispersions with an organopolysiloxane compound chosen, for example, from those described in WO 93/05762 or in WO 93/21316.

It can also be used to form cosmetically or physiologically acceptable acid-pH aqueous gels, such as those described in WO 93/07856; it can also be used in combination with nonionic celluloses, in order to form, for example, styling gels, such as those described in EP 0 684 024, or else in combination with fatty acid esters of a sugar, in order to form compositions for treating the hair or the skin, such as those described in EP 0 603 019, or alternatively in shampoos or conditioners as described and claimed in WO 92/21316, or, finally, in combination with an anionic homopolymer such as Carbopol™ in order to form hair treatment products, such as those described in DE 195 23596, or in combination with other thickening polymers.

The composition according to the invention is also compatible with active ingredients such as, for example, self-tanning agents, for instance dihydroxyacetone (DHA) and/or erythrulose, or anti-acne agents; it can therefore be introduced into self-tanning compositions such as those claimed in EP 0 715 845, EP 0 604 249, EP 0 576 188 or in WO 93/07902.

It is also compatible with N-acylated derivatives of amino acids, which allows it to be used in soothing compositions, in particular for sensitive skin, such as those described or claimed in WO 92/21318 or WO 94/27561 or in WO 98/09611.

When the composition as defined above is intended for hair treatment, it comprises more particularly an inverse latex of cationic polymer which is the subject of the present invention.

When the composition as defined above is intended for treatment of the skin and/or the mucous membranes, it comprises more particularly an inverse latex of anionic polymer which is the subject of the present invention.

The inverse latices which are the subject of the present invention can be used as a thickener for textile printing pastes.

The purpose of the examples which follow is to illustrate the present invention.

A) Examples of Preparation of a Composition According to the Invention

EXAMPLE 1

Preparation of an Inverse Latex of (AMPS, Na Salt)/HEA (90/10) Copolymer, Crosslinked with methylenebis(acrylamide), in dioctyl ether (Composition 1)

a)—The following are introduced into a beaker, with stirring:
 632.5 g of a commercial 55% sodium 2-methyl-2-[(1-oxo-2-propenyl)amino]-1-propanesulfonate (AMPS, Na salt) solution,
 19.6 g of (2-hydroxyethyl)acrylate (HEA),
 0.45 g of sodium diethylenetriaminepentaacetate,
 0.105 g of methylenebis(acrylamide).
The pH of this aqueous solution is equal to 4.
b)—An organic phase is prepared by mixing:
 240 g of dioctyl ether of plant origin,
 16.1 g of sorbitan isostearate (Montane™ 70),
 13.4 g of sorbitan monolaurate (Montane™ 20), and
 2.9 g of polyglyceryl polyhydroxystearate (Dehymul™ PGPH).
c)—The aqueous phase is gradually introduced into the organic phase and the whole is stirred vigorously by means of an Ultra-Turrax™ mixer sold by IKA. The emulsion obtained is then transferred into a polymerization reactor, subjected to sparging with nitrogen and then cooled to approximately 5-6° C. 2.5 ml of a solution containing 0.64% by weight of cumene hydroperoxide in dioctyl ether, and 0.134 g of sodium persulfate in 5 g of water are then added, followed, after homogenization of the solution, by an aqueous solution of sodium metabisulfite (0.8% in water) for approximately 60 minutes at a rate of approximately 0.15 ml/minute, while allowing the temperature to rise to the temperature at the end of polymerization. The reaction medium is then kept at this temperature for approximately 90 minutes. 3% of decaglyceryl monolaurate (Decaglyn™ 1L) are then added, and the desired water-in-oil emulsion is obtained.

Evaluation of the Properties

Viscosity in water at 3% of the latex (Brookfield RVT spindle 6, speed 5):

$\eta$=112000 mPa·s.

Viscosity at 3% of the latex in saline (0.1% NaCl) (Brookfield RVT spindle 3, speed 5): $\eta$=9580 mPa·s.

Viscosity of the latex at 25° C. (Brookfield RVT spindle 3, speed 20):

$\eta$=1800 mPa·s.

EXAMPLE 2

Preparation of an Inverse Latex of (AMPS, Na Salt)/HEA/THAM/AA (84/10/4/2) Tetrapolymer, Crosslinked with methylenebis(acrylamide), in dioctyl ether (Composition 2)

a)—The following are introduced into a beaker, with stirring:
 627.6 g of a commercial 55% sodium 2-methyl-2-[(1-oxo-2-propenyl)amino]-1-propanesulfonate (AMPS, Na salt) solution,
 20.8 g of (2-hydroxyethyl)acrylate (HEA),
 0.45 g of sodium diethylenetriaminepentaacetate (Versenex™ 80),
 12.6 g of tris(hydroxymethyl)acrylamidomethane (THAM),
 2.6 g of acrylic acid,
 0.028 g of methylenebis(acrylamide).
The pH of this aqueous solution is equal to 4.
b)—An organic phase is prepared by mixing:
 160 g of dioctyl ether of plant origin (Cosmacol™ OE),
 90 g of Isopar™ H,
 15 g of sorbitan isostearate (Montane™ 70),
 10 g of Hypermer™ 6212, and
 7.4 g of Blemmer™ PLE 200.
c)—The aqueous phase is gradually introduced into the organic phase and the whole is stirred vigorously by means of an Ultra-Turrax™ mixer sold by IKA. The emulsion obtained is then transferred into a polymerization reactor, subjected to sparging with nitrogen and then cooled to approximately 5-6° C. 2.5 ml of a solution containing 0.64% by weight of cumene hydroperoxide in dioctyl ether, and 0.134 g of sodium persulfate in 5 g of water are then added, followed, after homogenization of the solution, by an aqueous solution of sodium metabisulfite (0.8% in water) for approximately 60 minutes at a rate of approximately 0.15 ml/minute, while allowing the temperature to rise to the temperature at the end of polymerization. The reaction medium is then kept at this temperature for approximately 90 minutes. 5% of decaglyceryl monolaurate (Decaglyn™ 1L) are then added, and the desired water-in-oil emulsion is obtained.

Evaluation of the Properties

Viscosity of the self-invertible inverse latex at 25° C. (Brookfield RVT spindle 5, speed 20):

$\eta$=19800 mPa·s.

Viscosity in water at 2% of the self-invertible inverse latex (Brookfield RVT spindle 6, speed 5):

$\eta$=61600 mPa·s.

Viscosity in water (containing 0.1% sodium chloride) at 2% of the self-invertible inverse latex (Brookfield RVT spindle 4, speed 5):

$\eta$=26900 mPa·s pH at 2%: 5.5.

EXAMPLE 3

Preparation of an Inverse Latex of (AMPS, Na Salt)/HEA (90/10) Copolymer, Crosslinked with methylenebis(acrylamide), in dioctyl ether (Composition 3)

The procedure is carried out as described in example 1, replacing the 3% of decaglyceryl monolaurate (Decaglyn™ 1L) with 4% of sorbitan stearate polyethoxylated with 20 mol of ethylene oxide (Montanox™ 60). The desired water-in-oil emulsion is obtained.

Evaluation of the Properties

Viscosity in water at 3% of the latex (Brookfield RVT spindle 6, speed 5):

$\zeta$=107 000 mPa·s.

Viscosity at 3% of the latex in saline (0.1% NaCl) (Brookfield RVT spindle 3, speed 5): $\eta$=3 480 mPa·s.

Viscosity of the latex at 25° C. (Brookfield RVT spindle 4, speed 20):

$\eta$=3480 mPa·s.

EXAMPLE 4

Preparation of an Inverse Latex of (AMPS, Na Salt)/ N,N-dimethylacrylamide (DMAM)/Acrylic Acid (85/10/5) Terpolymer, Crosslinked with methylenebis(acrylamide), in dioctyl ether (Composition 3) 7994MP a)—The following are introduced into a beaker, with stirring:
- 624.5 g of a commercial 55% sodium 2-methyl-2-[(1-oxo-2-propenyl)amino]-1-propanesulfonate (AMPS, Na salt) solution,
- 17.5 g of N,N-dimethylacrylamide (DMAM),
- 0.45 g of sodium diethylenetriaminepentaacetate (Versenex™ 80),
- 6.5 g of acrylic acid,
- 0.027 g of methylenebis(acrylamide).

The pH of this aqueous solution is equal to 4.

b)—An organic phase is prepared by mixing:
- 160 g of dioctyl ether of plant origin (Cosmacol™ OE),
- 90 g of Isopar™ H,
- 17 g of sorbitan isostearate (Montane™ 70),
- 3 g of Hypermer™ 6212,
- 3.66 g of Blemmer™ PLE 200.

c)—The aqueous phase is gradually introduced into the organic phase and the whole is stirred vigorously by means of an Ultra-Turrax™ mixer sold by IKA. The emulsion obtained is then transferred into a polymerization reactor, subjected to sparging with nitrogen and then cooled to approximately 5-6° C. 2.5 ml of a solution containing 0.64% by weight of cumene hydroperoxide in dioctyl ether, and 0.3 g of sodium persulfate in 5 g of water, are then added, followed, after homogenization of the solution, by an aqueous solution of sodium metabisulfite (0.33% in water) for approximately 60 minutes at a rate of approximately 0.15 ml/minute, while allowing the temperature to rise to the temperature at the end of polymerization. The reaction medium is then kept at this temperature for approximately 90 minutes. 5% of heptaethoxylated lauryl alcohol (Simulsol™ P7) are then added, and the desired water-in-oil emulsion is obtained.

Evaluation of the Properties

Viscosity of the self-invertible inverse latex at 25° C. (Brookfield RVT spindle 3, speed 20):

$\eta$=610 mPa·s.

Viscosity in water at 3% of the self-invertible inverse latex (Brookfield RVT spindle 6, speed 5):

$\eta$=26800 mPa·s.

Viscosity in water (containing 0.1% sodium chloride) at 3% of the self-invertible inverse latex (Brookfield RVT spindle 4, speed 5):

$\eta$=15640 mPa·s.

EXAMPLE 5

Preparation of a Concentrated Self-invertible Inverse Latex of (AMPS, Na Salt)/N,N-dimethylacrylamide (DMAM)/Acrylic Acid (85/10/5) Terpolymer, Crosslinked with methylenebis(acrylamide), in dioctyl ether (Composition 3) 7994MP The procedure is carried out in the same way as in example 4 above, but evaporating after the addition of the Isopar™ H inverter. A self-invertible inverse latex comprising approximately 63% of terpolymer is obtained.

Evaluation of the Properties

Viscosity of the self-invertible inverse latex at 25° C. (Brookfield RVT spindle 3, speed 20):

$\eta$=1100 mPa·s.

Viscosity in water at 2% of the self-invertible inverse latex (Brookfield RVT spindle 6, speed 5):

$\eta$=32400 mPa·s.

Viscosity in water (containing 0.1% sodium chloride) at 2% of the self-invertible inverse latex (Brookfield RVT spindle 6, speed 5):

$\eta$=22000 mPa·s.

COMPARATIVE EXAMPLE 1

Preparation of an Inverse Latex of (AMPS, Na Salt)/HEA (90/10) Copolymer, Crosslinked with methylenebis(acrylamide), in C8-C10 triglyceride (Composition 1a)

a)—The following are introduced into a beaker, with stirring:
- 632.5 g of a commercial 55% sodium 2-methyl-2-[(1-oxo-2-propenyl)amino]-1-propanesulfonate (AMPS, Na salt) solution,
- 19.6 g of (2-hydroxyethyl)acrylate (HEA),
- 0.45 g of sodium diethylenetriaminepentaacetate,
- 0.105 g of methylenebis(acrylamide).

The pH of this aqueous solution is equal to 4.

b)—An organic phase is prepared by mixing:
- 240 g of C8-C10 triglyceride,
- 16.1 g of sorbitan isostearate (Montane™ 70),
- 13.4 g of sorbitan monolaurate (Montane™ 20), and
- 2.9 g of polyglyceryl polyhydroxystearate (Dehymul™ PGPH).

c)—The aqueous phase is gradually introduced into the organic phase and the whole is stirred vigorously by means of an Ultra-Turrax™ mixer sold by IKA. The emulsion obtained is then transferred into a polymerization reactor, subjected to sparging with nitrogen, and then cooled to approximately 5-6° C. 2.5 ml of a solution containing 0.64% by weight of cumene hydroperoxide in the C8-C10 triglyceride, and 0.134 g of sodium persulfate in 5 g of water, are then added, followed, after homogenization of the solution, by an aqueous solution of sodium metabisulfite (0.8% in water) at a rate of approximately 0.15 ml/minute, while allowing the temperature to rise. In the first few minutes following the addition of the cumene hydroperoxide, a large increase in temperature, and thickening of the reaction medium, which blocks the stirring, accompanied by settling out of the oily phase, are observed, thus characterizing the solidifying of the reaction medium. The desired inverse latex, with the C8-C10 triglyceride as oily phase, is not therefore obtained.

B) Properties of the Compositions According to the Invention

None of the inverse latices prepared as described in examples 1 to 5 cause accelerated sedimentation of the emulsions thickened by them. Furthermore, the oily phase used induces no blocking of the inversion, unlike what sometimes happens when this phase is a fatty acid ester.

C) Examples of Formulations Prepared with the Compositions According to the Invention

EXAMPLE 1

Aftershave Balm

Formula

| | | |
|---|---|---|
| A | Composition 1: | 1.5% |
| | Water: | q.s. 100% |
| B | Micropearl ™ M100: | 5.0% |
| | Sepicide ™ CI: | 0.50% |
| | Fragrance: | 0.20% |
| | 95° ethanol: | 10.0% |

Procedure
Add B to A.

EXAMPLE 2

Soothing Aftersun Care

Formula

| | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. 100% |
| Composition 1: | 2.50% |
| Sepicide ™ HB: | 0.3% |
| Sepicide ™ CI: | 0.2% |
| Fragrance: | 0.4% |
| Dye: | 0.03% |

EXAMPLE 3

Moisturizing and Matting Foundation

Formula

| | | |
|---|---|---|
| A | Water: | 20.0% |
| | Butylene glycol: | 4.0% |
| | PEG-400: | 4.0% |
| | Pecosil ™ PS100: | 1.0% |
| | Sodium hydroxide: | q.s. pH = 9 |
| | Titanium dioxide: | 7.0% |
| | Talc: | 2.0% |
| | Yellow iron oxide: | 0.8% |
| | Red iron oxide: | 0.3% |
| | Black iron oxide: | 0.05% |
| B | Lanol ™ 99: | 8% |
| | Caprylic capric triglyceride: | 8% |
| | Montanov ™ 202: | 5.00% |
| C | Water: | q.s. 100% |
| | Micropearl ™ M305: | 2.0% |
| | Tetrasodium EDTA: | 0.05% |
| D | Dow Corning ™ 345: | 4.0% |
| | Ketrol ™ T: | 0.2% |
| | Composition 1: | 0.8% |
| E | Sepicide ™ HB: | 0.5% |
| | Sepicide CI: | 0.3% |
| | Fragrance: | 0.2% |

Procedure
Prepare the mixtures B+D and A+C, at 80° C., and then mix and emulsify the whole.

EXAMPLE 4

Radiance Gel

Formula

| | | |
|---|---|---|
| A | Composition 1: | 4% |
| | Water: | 30% |
| B | Elastine HPM: | 5.0% |
| C | Micropearl ™ M100: | 3% |
| | Water: | 5% |
| D | Sepicide ™ CI: | 0.2% |
| | Sepicide ™ HB: | 0.3% |
| | Fragrance: | 0.06% |
| | 50% sodium pyrolidinonecarboxylate: | 1% |
| | Water: | q.s. 100% |

Procedure
Prepare A; add B, then C, then D.

EXAMPLE 5

Body Milk

Formula

| | |
|---|---|
| Montanov ™ S: | 3.5% |
| Lanol ™ 37T: | 8.0% |
| Solagum ™ L: | 0.05% |
| Water: | q.s. 100% |
| Eusolex ™ 4360: | 2.0% |
| Dimethicone 350 cPs: | 0.05% |
| Composition 4: | 0.8% |
| Preservative: | 0.2% |
| Fragrance: | 0.4% |

EXAMPLE 6

Makeup-removing Emulsion with Sweet Almond Oil

Formula

| | |
|---|---|
| Montanov ™ 68: | 5% |
| Sweet almond oil: | 5% |
| Water: | q.s. 100% |
| Composition 3: | 0.3% |
| Glycerol: | 5% |
| Preservative: | 0.2% |
| Fragrance: | 0.3% |

EXAMPLE 7

Moisturizing Cream for Greasy Skin

Formula

| | |
|---|---|
| Montanov ™ 68: | 5% |
| Cetylstearyl octanoate: | 8% |
| Octyl palmitate: | 2% |
| Water: | q.s. 100% |
| Composition 3: | 0.6% |

| | |
|---|---|
| Micropearl ™ M100: | 3.0% |
| Mucopolysaccharides: | 5% |
| Sepicide ™ HB: | 0.8% |
| Fragrance: | 0.3% |

EXAMPLE 8

Cream with AHA for Sensitive Skin

| | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | q.s. 100% |
| Composition 4: | 1.50% |
| Gluconic acid: | 1.50% |
| Triethanolamine: | 0.9% |
| Sepicide ™ HB: | 0.3% |
| Sepicide ™ CI: | 0.2% |
| Fragrance: | 0.4% |

EXAMPLE 9

Soothing Aftersun Care

| | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. 100% |
| Composition 2: | 2.50% |
| Sepicide ™ HB: | 0.3% |
| Sepicide ™ CI: | 0.2% |
| Fragrance: | 0.4% |
| Dye: | 0.03% |

EXAMPLE 10

Makeup-removing Milk

| | |
|---|---|
| Montanov ™ S: | 3% |
| Primol ™ 352: | 8.0% |
| Sweet almond oil: | 2% |
| Water: | q.s. 100% |
| Composition 5: | 0.8% |
| Preservative: | 0.2% |

EXAMPLE 11

Fluid emulsion at alkaline pH

| | |
|---|---|
| Marcol ™ 82: | 5.0% |
| NaOH: | 10.0% |
| Water: | q.s. 100% |
| Composition 4: | 1.5% |

EXAMPLE 12

Fluid Foundation

| | |
|---|---|
| Simulsol ™ 165: | 5.0% |
| Lanol ™ 84D: | 8.0% |
| Lanol ™ 99: | 5.0% |
| Water: | q.s. 100% |
| Mineral fillers and pigments: | 10.0% |
| Composition 5: | 1.2% |
| Preservative: | 0.2% |
| Fragrance: | 0.4% |

EXAMPLE 13

Antisun Milk

| | |
|---|---|
| Montanov ™ S: | 3.5% |
| Lanol ™ 37T: | 10.0% |
| Parsol ™ MCX: | 5.0% |
| Eusolex ™ 4360: | 2.0% |
| Water: | q.s. 100% |
| Composition 1: | 1.8% |
| Preservative: | 0.2% |
| Fragrance: | 0.4% |

EXAMPLE 14

Leave-on Care Composition

| | |
|---|---|
| Composition 3: | 1.5% |
| Fragrance: | q.s. |
| Preservative: | q.s. |
| Dow Corning ™ X2 8360: | 5.0% |
| Dow Corning ™ Q2 1401: | 15.0% |
| Water: | q.s. 100% |

EXAMPLE 15

Slimming Gel

| | |
|---|---|
| Composition 6: | 5% |
| Ethanol: | 30% |
| Menthol: | 0.1% |
| Caffeine: | 2.5% |
| Extracts of *ruscus*: | 2% |
| Extract of *ivy*: | 2% |
| Sepicide ™ HB: | 1% |
| Water | q.s. 100% |

EXAMPLE 16

Ultra-natural Tinted Cream Gel

Formula

| | | | |
|---|---|---|---|
| A | Water: | | 10.0% |
| | Butylene glycol: | | 4.0% |
| | PEG-400: | | 4.0% |
| | Pecosil ™ PS100: | | 1.5% |
| | NaOH: | | q.s. pH = 7 |
| | Titanium dioxide: | | 2.0% |

EXAMPLE 17

Care for Greasy Skin

Formula

|   |   |   |
|---|---|---|
| A | Micropearl ™ M310 | 1.0% |
|   | Composition 5: | 5.0% |
|   | Octyl isononanoate: | 4.0% |
| B | Water: | q.s. 100% |
| C | Sepicontrol ™ A5: | 4.0% |
|   | Fragrance: | 0.1% |
|   | Sepicide ™ HB: | 0.3% |
|   | Sepicide ™ CI: | 0.2% |
| D | Capigel ™ 98: | 0.5% |
|   | Water: | 10% |

(continued from previous page)

|   |   |   |
|---|---|---|
|   | Yellow iron oxide: | 0.8% |
|   | Red iron oxide: | 0.3% |
|   | Black iron oxide: | 0.05% |
| B | Lanol ™ 99: | 4.0% |
|   | Caprylic capric triglyceride | 4.0% |
|   | Sepifeel ™ One: | 1.0% |
|   | Composition 5: | 3.0% |
| C | Water: | q.s. 100% |
|   | Micropearl ™ M305: | 2.0% |
|   | Tetrasodium EDTA: | 0.05% |
|   | Dow Corning ™ 245 Fluid: | 4.0% |
| D | Sepicide ™ HB: | 0.5% |
|   | Sepicide ™ CI: | 0.3% |
|   | Fragrance: | 0.2% |

Procedure

Prepare the mixture B+C, then add A, then D.

EXAMPLE 18

Cream with AHA

Formula

|   |   |   |
|---|---|---|
| A | Montanov ™ 68: | 5.0% |
|   | Lipacide ™ PVB: | 1.05% |
|   | Lanol ™ 99: | 10.0% |
| B | Water: | q.s. 100% |
|   | Gluconic acid: | 1.5% |
|   | TEA (triethanolamine): | 0.9% |
| C | Composition 4: | 1.5% |
| D | Fragrance: | 0.4% |
|   | Sepicide ™ HB: | 0.2% |
|   | Sepicide ™ CI: | 0.4% |

EXAMPLE 19

Nongreasy Self-tanning Product for the Face and body

Formula

|   |   |   |
|---|---|---|
| A | Lanol ™ 2681: | 3.0% |
|   | Composition 3: | 2.5% |
| B | Water: | q.s. 100% |
|   | Dihydroxyacetone: | 3.0% |
| C | Fragrance: | 0.2% |
|   | Sepicide ™ HB: | 0.8% |
|   | NaOH (sodium hydroxide): | q.s. pH = 5 |

EXAMPLE 20

Antisun Milk with Monoi de Tahiti Oil

Formula

|   |   |   |
|---|---|---|
| A | Monoi de Tahiti oil: | 10% |
|   | Lipacide ™ PVB: | 0.5% |
|   | Composition 7: | 2.2% |
| B | Water: | q.s. 100% |
| C | Fragrance: | 0.1% |
|   | Sepicide ™ HB: | 0.3% |
|   | Sepicide ™ CI: | 0.1% |
|   | Parsol ™ MCX: | 4.0% |

EXAMPLE 21

Facial Antisun Care

Formula

|   |   |   |
|---|---|---|
| A | DC ™ 1501: | 4.0% |
|   | Composition 5: | 3.5% |
| B | Water: | q.s. 100% |
| C | Fragrance: | 0.1% |
|   | Sepicide ™ HB: | 0.3% |
|   | Sepicide ™ CI: | 0.21% |
|   | Parsol ™ MCX: | 5.0% |
|   | Titanium mica: | 2.0% |
|   | Lactic acid: | q.s. pH = 6.5 |

EXAMPLE 22

No-sun Tanning Emulsion

Formula

|   |   |   |
|---|---|---|
| A | Lanol ™ 99: | 15% |
|   | Montanov ™ 68: | 5.0% |
|   | Parsol ™ MCX: | 3.0% |
| B | Water: | q.s. 100% |
|   | Dihydroxyacetone: | 5.0% |
|   | Monosodium phosphate: | 0.2% |
| C | Composition 1: | 0.5% |
| D | Fragrance: | 0.3% |
|   | Sepicide ™ HB: | 0.8% |
|   | NaOH: | q.s. pH = 5 |

EXAMPLE 23

Care Cream

|   |   |   |
|---|---|---|
|   | Dow Corning ™ 345: | 10% |
|   | Composition 8: | 0.8% |
|   | Montanov ™ 68: | 4.5% |
|   | Preservative: | 0.65% |

-continued

| | |
|---|---|
| Lysine: | 0.025% |
| EDTA (disodium salt): | 0.05% |
| Ketrol ™ T: | 0.2% |
| Glycerol: | 3.0% |
| Water: | q.s. 100% |

EXAMPLE 24

Care Cream

| | |
|---|---|
| Dow Corning ™ 345: | 10% |
| Composition 3: | 0.8% |
| Montanov ™ 68: | 4.5% |
| Perfluoropolymethyl isopropyl ether: | 0.5% |
| Preservative: | 0.65% |
| Lysine: | 0.025% |
| EDTA (disodium salt): | 0.05% |
| Pemulen ™ TR: | 0.2% |
| Glycerol: | 3% |
| Water: | q.s. 100% |

EXAMPLE 25

Body Milk

Formula

| | | |
|---|---|---|
| A | Simulsol ™ 165: | 5.0% |
| | Lanol ™ 1688: | 12.0% |
| | Lanol ™ 14 M: | 2.0% |
| | Cetyl alcohol: | 0.3% |
| | Schercemol ™ OP: | 3% |
| B | Water: | q.s. 100% |
| C | Composition 4: | 0.35% |
| D | Sepicide ™ CI: | 0.2% |
| | Sepicide ™ HB: | 0.5% |
| | Fragrance: | 0.20% |

Procedure

Emulsify B in A at about 75° C.; add C at about 60° C. and then D at about 30° C.

EXAMPLE 26

Body Milk

Formula

| | | |
|---|---|---|
| A | Montanov ™ S: | 3.0% |
| | Glyceryl triheptonate: | 10.0% |
| B | Water: | q.s. 100% |
| C | Composition 4: | 1.0% |
| D | Fragrance: | q.s. |
| | Preservative: | q.s. |

Procedure

Melt A at about 75° C. Emulsify B in A at 75° C.; add C at about 60° C., then D.

EXAMPLE 27

Alcohol-free Soothing Aftershave Balm

| | |
|---|---|
| Mixture of lauryl amino acids: | 0.1% to 5% |
| Magnesium potassium aspartate: | 0.002% to 0.5% |
| Lanol ™ 99: | 2% |
| Sweet almond oil: | 0.5% |
| Water: | q.s. 100% |
| Composition 3: | 3% |
| Sepicide ™ HB: | 0.3% |
| Sepicide ™ CI: | 0.2% |
| Fragrance: | 0.4% |

EXAMPLE 28

Satin Body Emulsion

Formula

| | | |
|---|---|---|
| A | Simulsol ™ 165: | 5.0% |
| | Lanol ™ 1688: | 8.50% |
| | Shea butter: | 2% |
| | Liquid paraffin: | 6.5% |
| | Lanol ™ 14 M: | 3% |
| | Lanol ™ S: | 0.6% |
| B | Water: | 66.2% |
| C | Micropearl ™ M100: | 5% |
| D | Composition 5: | 3% |
| E | Sepicide ™ CI: | 0.3% |
| | Sepicide ™ HB: | 0.5% |
| | Monteine ™ CA: | 1% |
| | Fragrance: | 0.20% |
| | Vitamin E acetate: | 0.20% |
| | Sodium pyrolidinonecarboxylate: | 1% (moisturizer) |

Procedure

Add C to B, emulsify B in A at 70° C., then add D at 60° C., and then E at 30° C.

EXAMPLE 29

O/W cream

Formula

| | | |
|---|---|---|
| A | Simulsol ™ 165: | 5.0% |
| | Lanol ™ 1688: | 20.0% |
| | Lanol ™ P: | 1.0% |
| B | Water: | q.s. 100% |
| C | Composition 2: | 2.50% |
| D | Sepicide ™ CI: | 0.20% |
| | Sepicide ™ HB: | 0.30% |

Procedure

Introduce B into A at about 75° C.; add C at about 60° C., then D at about 45° C.

EXAMPLE 30

Nongreasy Antisun Gel

Formula

| A | Composition 5: | 3.00% |
|---|---|---|
|   | Water: | 30% |
| B | Sepicide ™ C: | 0.20% |
|   | Sepicide ™ HB: | 0.30% |
|   | Fragrance: | 0.10% |
| C | Dye: | q.s. |
|   | Water: | 30% |
| D | Micropearl ™ M100: | 3.00% |
|   | Water: | q.s. 100% |
| E | Silicone oil: | 2.0% |
|   | Parsol ™ MCX: | 5.00% |

Procedure
Introduce B into A; add C, then D, then E.

EXAMPLE 31

Antisun Milk

Formula

| A | Montanov ™ S: | 3.0% |
|---|---|---|
|   | Sesame oil: | 5.0% |
|   | Parsol ™ MCX: | 5.0% |
|   | λ-carrageenan: | 0.10% |
| B | Water: | q.s. 100% |
| C | Composition 3: | 0.80% |
| D | Fragrance: | q.s. |
|   | Preservative: | q.s. |

Procedure
Emulsify B in A at 75° C., then add C at about 60° C., then D at about 30° C., and adjust the pH if necessary.

EXAMPLE 32

Massage Gel

Formula

| A | Composition 2: | 3.5% |
|---|---|---|
|   | Water: | 20.0% |
| B | Dye: | 2 drops/100 g |
|   | Water: | q.s. |
| C | Alcohol: | 10% |
|   | Menthol: | 0.10% |
| D | Silicone oil: | 5.0% |

Procedure
Add B to A; then add C to the mixture, then D.

EXAMPLE 33

Massage Care Gel

Formula

| A | Composition 3: | 3.00% |
|---|---|---|
|   | Water: | 30% |
| B | Sepicide ™ CI: | 0.20% |
|   | Sepicide ™ HB: | 0.30% |
|   | Fragrance: | 0.05% |
| C | Dye: | q.s. |
|   | Water: | q.s. 100% |
| D | Micropearl ™ SQL: | 5.0% |
|   | Lanol ™ 1688: | 2% |

Procedure
Prepare A; add B, then C, then D.

EXAMPLE 34

Alcohol-free Soothing Aftershave Balm

Formula

| A | Lipacide ™ PVB: | 1.0% |
|---|---|---|
|   | Lanol ™ 99: | 2.0% |
|   | Sweet almond oil: | 0.5% |
| B | Composition 1: | 3.5% |
| C | Water: | q.s. 100% |
| D | Fragrance: | 0.4% |
|   | Sepicide ™ HB: | 0.4% |
|   | Sepicide ™ CI: | 0.2% |

EXAMPLE 35

Refreshing Aftershave Gel

Formula

| A | Lipacide ™ PVB: | 0.5% |
|---|---|---|
|   | Lanol ™ 99: | 5.0% |
|   | Composition 3: | 2.5% |
| B | Water: | q.s. 100% |
| C | Micropearl ™ LM: | 0.5% |
|   | Fragrance: | 0.2% |
|   | Sepicide ™ HB: | 0.3% |
|   | Sepicide ™ CI: | 0.2% |

EXAMPLE 36

Gloss Gel

| Composition 7: | 1.5% |
|---|---|
| Volatile silicone: | 25% |
| Propylene glycol: | 25% |
| Demineralized water: | 10% |
| Glycerol: | q.s. 100% |

EXAMPLE 37

Slimming Gel

| Composition 6: | 1.5% |
|---|---|
| Lanol ™ 99: | 2% |
| Caffeine: | 5% |
| Ethanol: | 40% |
| Micropearl ™ LM: | 2% |
| Demineralized water: | q.s. 100% |
| Preservative, fragrance: | q.s. |

EXAMPLE 38

Makeup-removing Milk

| | |
|---|---|
| Simulsol ™ 165: | 4% |
| Montanov ™ 202: | 1% |
| Triglyceride caprylate-caprate: | 15% |
| Pecosil ™ DCT: | 1% |
| Demineralized water: | q.s. |
| Capigel ™ 98: | 0.5% |
| Composition 4: | 1% |
| Proteol ™ APL: | 2% |
| Sodium hydroxide: | q.s. pH = 7 |

EXAMPLE 39

Restructuring "Rinse-off" Cream Mask for Stressed and Embrittled Hair

| | |
|---|---|
| Ketrol ™ T: | 0.5% |
| Pecosil ™ SPP50: | 0.75% |
| N-cocoyl amino acids: | 0.70% |
| Butylene glycol: | 3.0% |
| Composition 1: | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | q.s. 100% |

EXAMPLE 40

Antisun Cream

| | |
|---|---|
| Simulsol ™ 165: | 3% |
| Montanov ™ 202: | 2% |
| C12-C15 benzoate: | 8% |
| Pecosil ™ PS 100: | 2% |
| Dimethicone: | 2% |
| Dow Corning ™ 345: | 5% |
| Parsol ™ MCX: | 6% |
| Eusolex ™ 4360: | 4% |
| Titanium oxide: | 8% |
| Ketrol ™ T: | 0.2% |
| Butylene glycol: | 5% |
| Demineralized water: | q.s. 100% |
| Composition 1: | 1.5% |
| Preservative, fragrance: | q.s. |

EXAMPLE 41

Care Gel for Combination Skin

| | |
|---|---|
| Composition 1: | 4% |
| Plant squalane: | 5% |
| Dimethicone: | 1.5% |
| Sepicontrol ™ A5: | 4% |
| Ketrol ™ T: | 0.3% |
| Water: | q.s. 100% |
| Preservative, fragrance: | q.s. |

EXAMPLE 42

Hair Lotion

| | |
|---|---|
| Butylene glycol: | 3.0% |
| Composition 4: | 3% |
| Simulsol ™ 1293: | 3.0% |
| Lactic acid: | q.s. pH = 6 |
| Sepicide ™ HB: | 0.2% |
| Sepicide ™ CI: | 0.3% |
| Fragrance: | 0.3% |
| Water | q.s. 100% |

EXAMPLE 43

Protective, Relaxing Shampoo

| | |
|---|---|
| Amonyl ™ 675 SB: | 5.0% |
| 28% sodium lauryl ether sulfate: | 35.0% |
| Composition 1: | 3.0% |
| Sepicide ™ HB: | 0.5% |
| Sepicide ™ CI: | 0.3% |
| Sodium hydroxide: | q.s. pH = 7.2 |
| Fragrance: | 0.3% |
| Dye (FDC blue 1/yellow 5): | q.s. |
| Water: | q.s. 100% |

EXAMPLE 44

"Leave-on" Protective Product; Antistress Haircare

| | |
|---|---|
| Ketrol ™ T: | 0.5% |
| Mixture of cocoyl amino acids: | 3.0% |
| Buylene glycol: | 5.0% |
| DC 1501: | 5.0% |
| Composition 1: | 4.0% |
| Sepicide ™ HB: | 0.5% |
| Sepicide ™ CI: | 0.3% |
| Fragrance: | 0.3% |
| Water: | q.s. 100% |

EXAMPLE 45

Cream with Vitamins

| | |
|---|---|
| Simulsol ™ 165: | 5% |
| Montanov ™ 202: | 1% |
| Caprylic/capric triglycerides: | 20% |
| Vitamin A palmitate: | 0.2% |
| Vitamin E acetate: | 1% |
| Micropearl ™ M 305: | 1.5% |
| Composition 1: | 2% |
| Water: | q.s. 100% |
| Preservative, fragrance: | q.s. |

EXAMPLE 46

Antisun Gel

Formula

| | |
|---|---|
| Composition 1: | 3.00% |
| Sepicide ™ CI: | 0.20% |
| Sepicide ™ HB: | 0.30% |
| Fragrance: | 0.10% |
| Dye: | q.s. |
| Silica: | 3.00% |
| Water: | q.s. 100% |
| Silicone oil: | 2.0% |
| Eusolex ™ 4360: | 5.00% |

EXAMPLE 47

Lip Gloss

| | |
|---|---|
| Composition 1: | 1.50% |
| Schermol ™ TISC: | 15.00% |
| Vistanol ™ NPGC: | 15.00% |
| Candurin ™ Paprika: | 0.50% |
| Montanox ™ 80: | 1.00% |
| Antaron ™ V216: | 0.90% |
| Apricot flavoring: | 0.20% |
| Sepicide ™ HB: | 0.50% |
| C Maltidex ™ H16322: | q.s. 100% |

EXAMPLE 48

Sun Soil Pressed Powder

| | |
|---|---|
| Composition 1: | 2.00% |
| Lanol ™ 99: | 12.00% |
| Sepiwhite ™ MSH: | 1.00% |
| Talc: | 33.00% |
| Micropearl ™ M310: | 3.00% |
| Yellow iron oxide: | 0.80% |
| Red iron oxide: | 0.30% |
| Black iron oxide: | 0.05% |
| Mica: | q.s. 100% |

EXAMPLE 49

Emulsion for Atopic-prone Skin

| | |
|---|---|
| Arlacel ™ P135: | 2.00% |
| Composition 1: | 1.00% |
| Lanol ™ 1688: | 14.00% |
| Primol ™ 352: | 8.00% |
| Glycerol: | 5.00% |
| Water: | q.s. 100% |
| Magnesium sulfate: | 0.70% |
| Sepicide ™ HB: | 0.30% |
| Sepicide ™ CI: | 0.20% |
| Micropearl ™ M310: | 5.00% |

EXAMPLE 50

Soothing Antisun Care (Water-in-Silicone)

| | |
|---|---|
| Composition 1: | 2.00% |
| DC5225C: | 20.00% |
| DC345: | 10.00% |
| Sepicalm ™ VG: | 3.00% |
| Titanium dioxide MT100VT: | 5.00% |
| Zinc oxide Z-Cote HP1: | 5.00% |
| Sepicide ™ HB: | 0.30% |
| Fragrance: | 0.05% |
| Sepicide ™ CI: | 0.20% |
| Glycerol: | 5.00% |
| Sodium chloride: | 2.00% |
| Water: | q.s. 100% |

EXAMPLE 51

Multiphase Care

| | |
|---|---|
| Composition 1: | 3.00% |
| C12-15 alkyl benzoate: | 25.00% |
| Aquaxyl ™: | 3.00% |
| Sepitonic ™ M3: | 1.00% |
| Sepicide ™ HB: | 0.50% |
| Sepicide ™ CI: | 0.30% |
| Water: | q.s. 100% |

The definitions of the commercial products used in the examples are the following:

Amonyl™ 675 SB is a cocoamidopropyl hydroxy sultaine, sold by the company SEPPIC.

Antaron™ V216 is a synthetic polymer (PVP/hexadecene copolymer) distributed by the company UNIVAR.

Aquaxyl™ is a moisturizer sold by the company SEPPIC.

Arlacel™ P135 No, it is a product sold by Uniquema (now Croda). The SEPPIC equivalent is Simaline IE 200 SF, which is a PEG-30 dipolyhydroxystearate sold by the company SEPPIC.

C Maltidex™ H16322 is a polyol (maltitol syrup) sold by the company Cerestar.

Candurin Paprika is a mixture of potassium aluminum silicate and of iron oxide.

Capigel™ 98 is an acrylate copolymer-based liquid thickener sold by the company SEPPIC.

Dow Corning™ 245 Fluid is cyclomethicone, sold by the company Dow Corning.

DC 345 is a cyclomethicone sold by the company Dow Corning.

DC 5225C is a mixture of cyclopentasiloxane and dimethicone copolyol sold by the company Dow Corning.

DC1501 is a mixture of cyclopentasiloxane and dimethiconol sold by the company Dow Chemical.

Eusolex™ 4360 is benzophenone-3 sold by the company Merck.

Ketrol™ T is xanthan gum sold by the company Kelco.

Lanol™ 2681 is a mixture of coconut caprylate/caprate sold by the company SEPPIC.

Lanol™ 99 is isononyl isononanoate sold by the company SEPPIC.

Lanol™ 1688 is an emollient ester with a nongreasy effect sold by the company SEPPIC.

Lanol™ 14M and Lanol® S are consistency factors sold by the company SEPPIC.

Lanol™ 37T is glyceryl triheptanoate sold by the company SEPPIC.

Lanol™ 84D is dioctyl malate sold by the company SEPPIC.

Lanol™ P is an additive with a stabilizing effect sold by the company SEPPIC.

Lipacide™ PVB is a palmitoylated wheat protein hydrolysate sold by the company SEPPIC.

Marcol™ 82 is a liquid paraffin sold by the company ESSO.

Micropearl™ M100 is an ultrafine powder with a very soft feel and a matting action, sold by the company Matsumo.

Micropearl™ SQL is a mixture of microparticles containing squalane which is released by the action of massaging; it is sold by the company Matsumo.

Micropearl™ LM is a mixture of squalane, poly(methyl methacrylate) and menthol, sold by the company SEPPIC.

Micropearl™ M 305 is a silky water-dispersible powder based on a crosslinked methyl methacrylate copolymer.

Micropearl™ M310 is an ultrafine powder with a very soft feel and a matting action, sold by the company Matsumoto.

Montanox™ S is a pearlescent agent, sold by the company SEPPIC, based on a mixture of alkyl polyglucosides such as those described in WO 95/13863.

Montanox™ 202 (arachidyl glucoside, arachidyl alcohol+ behenyl alcohol) is a self-emulsifying composition such as those described in WO 98/17610, sold by the company SEPPIC.

Montanox™ 82 is an emulsifier based on cetearyl alcohol and cocoylglucoside.

Montanox™ 68 is a self-emulsifying composition based on cetearyl glucoside and cetearyl alcohol, as described in WO 92/06778, sold by the company SEPPIC.

Montanox™ 80 is sorbitan oleate polyethoxylated with 20 mol of ethylene oxide, sold by the company SEPPIC.

Monteine™ CA is a moisturizer sold by the company SEPPIC.

MT100VT is a micronized titanium dioxide that has undergone a surface treatment (aluminum hydroxide/stearic acid), distributed by the company Unipex.

Parsol™ MCX is octyl para-methoxycinnamate, sold by the company Givaudan.

Parsol NOX™ is a sunscreen sold by the company Givaudan.

Pecosil™ PS100 is dimethicone copolyol phosphate sold by the company Phoenix.

Pemulen™ TR is an acrylic polymer sold by Goodrich.

Primol™ 352 is a mineral oil sold by the company Exxon.

Proteol™ APL is a foaming surfactant sold by the company SEPPIC.

Schercemol™ OP is an emollient ester with a nongreasy effect.

Schercemol™ TISC is an ester (triisostearyl citrate) sold by the company Scher.

Sepicalm™ VG is a soothing active agent (sodium palmitoyl proline) sold by the company SEPPIC.

Sepitonic™ M3, which is a mixture of magnesium aspartate, zinc gluconate and copper gluconate, is an energizing active agent sold by the company SEPPIC.

Sepicontrol™ AS is a mixture of capryloyl glycine, sarcosine and extract of Cinnamonum zylanicum, sold by the company SEPPIC, such as those described in international patent application PCT/FR98/01313 filed on Jun. 23, 1998.

Sepicide™ CI, imidazolidinyl urea, is a preservative sold by the company SEPPIC.

Sepicide™ HB, which is a mixture of phenoxyethanol, methylparaben, ethylparaben, propylparaben and butylparaben, is a preservative sold by the company SEPPIC.

Sepifeel™ One is a mixture of palmitoyl proline, magnesium palmitoyl glutamate and magnesium palmitoyl sarcosinate, such as those described in FR 2787323.

Sepiwhite™ MSH is a depigmenting active agent (undecylenoyl phenylalanine) sold by the company SEPPIC.

Simulsol™ 1293 is hydrogenated and ethoxylated castor oil, with an ethoxylation index equal to 40, sold by the company SEPPIC.

Simulsol™ 165 is self-emulsifiable glyceryl stearate sold by the company SEPPIC.

Solagum™ L is a carrageenan sold by the company SEPPIC.

Vistanol™ NPGC is an ester (neopentyl glycol dicaprate) sold by the company Sewa Kasei.

Z-Cote HP1 is a micronized zinc oxide that has undergone a surface treatment, distributed by Gattefosse.

The invention claimed is:

1. A composition in the form of an inverse latex comprising, for 100% of its mass:
   a) from 10% by mass to 80% by mass of a linear, branched or crosslinked polymer (P) of 2-methyl-2-[(1-oxo-2-propenyl)amino]-1-propanesulfonic acid (also known as 2-acrylamido-2-methylpropanesulfonic acid) which is partially or totally salified, and optionally one or more monomers chosen from acrylic acid, methacrylic acid, itaconic acid, maleic acid or 3-methyl-3-[(1-oxo-2-propenyl)amino]butanoic acid, said monomers being free, partially salified or totally salified, acrylamide, methacrylamide, diacetone acrylamide, N,N-dimethylacrylamide, N-isopropyl-acrylamide, N-[2-hydroxy-1,1-bis (hydroxymethyl)-ethyl]propenamide [or tris (hydroxymethyl)acrylamido-methane or N-tris (hydroxymethyl)methylacrylamide also known as THAM], (2-hydroxyethyl) acrylate, (2,3-dihydroxypropyl) acrylate, (2-hydroxyethyl) methacrylate, (2,3-dihydroxypropyl) methacrylate, an ethoxylated derivative, of molecular weight between 400 and 1000, of each of these esters or vinylpyrrolidone; 2,N,N,N-tetramethyl-2-[(1-oxo-2-propenyl)amino]propanammonium chloride, bromide or iodide, 2,N,N-trimethyl-2-[(1-oxo-2-propenyl)amino]-propanammonium chloride, bromide or iodide, N,N,N-trimethyl-2-[(1-oxo-2-propenyl)oxy] ethanammonium chloride, bromide or iodide, N,N,N-trimethyl-3-[(1-oxo-2-propenyl)oxy]propanammonium chloride, bromide or iodide, N,N,N-trimethyl-2-[(1-oxo-2-propenyl)-amino]propanammonium chloride, bromide or iodide, or diallyldimethylammonium chloride, bromide or iodide;
   b) from 5% by mass to 10% by mass of an emulsifying system ($S_1$) of water-in-oil (W/O) type,
   c) from 1% by mass to 50% by mass of water,
   d) from 5% by mass to 50% by mass of at least one compound chosen from the compounds of formula (I):

$$R_1-O-R_2 \qquad (I),$$

in which $R_1$ and $R_2$ represent, independently of one another, a linear or branched alkyl radical containing from 5 to 18 carbon atoms, selected from the group consisting of dioctyl ether, didecyl ether, didodecyl ether, dodecyl octyl ether, dihexadecyl ether, (1,3-dimethylbutyl) tetradecyl ether, (1,3-dimethylbutyl)hexadecyl ether, bis(1,3-dimethylbutyl)ether and dihexyl ether.

2. The composition as defined in claim 1, wherein the polymer (P) is crosslinked.

3. The composition as defined in claim 1, further comprising:
   e) up to 5% by mass of an emulsifying system ($S_2$) of oil-in-water (O/W) type.

4. The composition as defined in claim 1, comprising from 20% by mass to 70% by mass of said polymer (P).

5. The composition as defined in claim 1, wherein the compound of formula (I) is dioctyl ether.

6. The composition as defined in claim 1, wherein the polymer (P) is selected from the group consisting of:
- a homopolymer of 2-methyl-2-[(1-oxo-2-propenyl)-amino]-1-propanesulfonic acid partially or totally salified in the form of a sodium salt or of an ammonium salt;
- a copolymer of 2-methyl-2-[(1-oxo-2-propenyl)amino]-1-propanesulfonic acid, partially or totally salified in the form of a sodium salt or an ammonium salt, and of (2-hydroxyethyl)acrylate;
- a copolymer of 2-methyl-2-[(1-oxo-2-propenyl)amino]-1-propanesulfonic acid and of acrylic acid partially or totally salified in the form of a sodium salt or of an ammonium salt;
- a copolymer of 2-methyl-2-[(1-oxo-2-propenyl)amino]-1-propanesulfonic acid partially or totally salified in the form of a sodium salt or of an ammonium salt, and of acrylamide;
- a copolymer of 2-methyl-2-[(1-oxo-2-propenyl)amino]-1-propanesulfonic acid partially or totally salified in the form of a sodium salt or of an ammonium salt, and of N,N-dimethylacrylamide;
- a terpolymer of 2-methyl-2-[(1-oxo-2-propenyl)amino]-1-propanesulfonic acid partially or totally salified in the form of a sodium salt or of an ammonium salt, of acrylamide and of vinylpyrrolidone;
- a terpolymer of 2-methyl-2-[(1-oxo-2-propenyl)amino]-1-propanesulfonic acid partially or totally salified in the form of a sodium salt or of an ammonium salt, of acrylic acid partially or totally salified in the form of a sodium salt or of an ammonium salt, and of acrylamide;
- a terpolymer of 2-methyl-2-[(1-oxo-2-propenyl)amino]-1-propanesulfonic acid partially or totally salified in the form of a sodium salt or of an ammonium salt, of acrylic acid partially or totally salified in the form of a sodium salt or of an ammonium salt, and of N,N-dimethylacrylamide; and
- a tetrapolymer of 2-methyl-2-[(1-oxo-2-propenyl)-amino]-1-propanesulfonic acid partially or totally salified in the form of a sodium salt or of an ammonium salt, of (2-hydroxyethyl) acrylate, of acrylic acid partially or totally salified in the form of a sodium salt or of an ammonium salt, and of N-[2-hydroxy-1,1-bis(hydroxymethyl)ethyl]propenamide.

7. The composition as defined in claim 6, wherein the polymer (P) is selected from the group consisting of:
- a crosslinked copolymer of 2-methyl-2-[(1-oxo-2-propenyl)amino]-1-propanesulfonic acid (a) partially or totally salified in the form of a sodium salt, and of (2-hydroxyethyl) acrylate (b), in an (a)/(b) molar ratio between 40/60 and 90/10;
- a crosslinked copolymer of 2-methyl-2-[(1-oxo-2-propenyl)amino]-1-propanesulfonic acid (a) partially or totally salified in the form of a sodium salt, and of acrylic acid (c) partially or totally salified in the form of a sodium salt, in an (a)/(c) molar ratio between 40/60 and 90/10;
- a crosslinked copolymer of 2-methyl-2-[(1-oxo-2-propenyl)amino]-1-propanesulfonic acid (a) partially or totally salified in the form of a sodium salt, and of acrylamide (b), in an (a)/(d) molar ratio between 40/60 and 90/10;
- a crosslinked copolymer of 2-methyl-2-[(1-oxo-2-propenyl)amino]-1-propanesulfonic acid (a) partially or totally salified in the form of a sodium salt, and of N,N-dimethylacrylamide (e), in an (a)/(e) molar ratio between 40/60 and 90/10;
- a crosslinked terpolymer of 2-methyl-2-[(1-oxo-2-propenyl)amino]-1-propanesulfonic acid (a) partially or totally salified in the form of a sodium salt, of acrylamide (d) and of vinylpyrrolidone (f), in an (a)/[(d)+(f)] molar ratio between 40/60 and 90/10;
- a crosslinked terpolymer of 2-methyl-2-[(1-oxo-2-propenyl)amino]-1-propanesulfonic acid (a) partially or totally salified in the form of a sodium salt, of acrylic acid (c) partially or totally salified in the form of a sodium salt, and of acrylamide (d), in an (a)/[(c)+(d)] molar ratio between 40/60 and 90/10;
- a crosslinked terpolymer of 2-methyl-2-[(1-oxo-2-propenyl)amino]-1-propanesulfonic acid (a) partially or totally salified in the form of a sodium salt, of acrylic acid (c) partially or totally salified in the form of a sodium salt, and of N,N-dimethylacrylamide (e), in an (a)/(e) molar ratio between 40/60 and 90/10; and
- a crosslinked tetrapolymer of 2-methyl-2-[(1-oxo-2-propenyl)amino]-1-propanesulfonic acid (a) partially or totally salified in the form of a sodium salt, of (2-hydroxyethyl)acrylate (b), of acrylic acid (c) partially or totally salified in the form of a sodium salt, and of N-[2-hydroxy-1,1-bis(hydroxymethyl)-ethyl]propenamide (g), in an (a)/[(b)+(c)+(g)] molar ratio between 40/60 and 90/10.

8. Method of using the composition as defined in claim 1, for preparing a cosmetic, dermopharmaceutical or pharmaceutical topical composition.

9. A topical composition, comprising, as thickener, between 0.1% and 10% by weight of the composition as defined in claim 1.

* * * * *